(12) United States Patent
Hirayama et al.

(10) Patent No.: US 6,955,812 B2
(45) Date of Patent: Oct. 18, 2005

(54) HEALTH FOOD AND PREPARATION HAVING AN ANTI-OBESITY EFFECT

(75) Inventors: Shin Hirayama, Yokohama (JP); Ryohei Ueda, Yokohama (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/616,921

(22) Filed: Jul. 11, 2003

(65) Prior Publication Data

US 2003/0228348 A1 Dec. 11, 2003

Related U.S. Application Data

(63) Continuation of application No. 10/186,702, filed on Jul. 2, 2002, now abandoned.

(30) Foreign Application Priority Data

Jul. 26, 2001 (JP) .................................... 2001-226298
Nov. 19, 2001 (JP) .................................... 2001-353609

(51) Int. Cl.$^7$ ............................................... A61K 35/78
(52) U.S. Cl. ................. 424/195.17; 514/517; 514/665; 514/667
(58) Field of Search ..................... 424/195.17; 514/517, 514/665, 667

(56) References Cited

U.S. PATENT DOCUMENTS

| | | | |
|---|---|---|---|
| 4,220,653 A | * | 9/1980 | Vivino |
| 4,820,527 A | | 4/1989 | Christensen |

FOREIGN PATENT DOCUMENTS

| | | |
|---|---|---|
| JP | 58-149666 A | 9/1983 |
| JP | 62-205020 | 9/1987 |
| JP | 03118319 A2 * | 5/1991 |
| JP | 4-266822 | 9/1992 |
| JP | 6-9422 A | 1/1994 |
| JP | 2001-46051 | 2/2001 |
| JP | 2002-20280 | 1/2002 |

OTHER PUBLICATIONS

English translation of JP 2001046501 (Feb. 20, 2001).*
B. Wickberg, Acta Chemica Scandinavica, vol. 11, No. 3, pp. 506–511, "Isolation of 2–L–Amino–3–Hydroxy–1–Propane Sulphonic Acid from Polysiphonia Fastigiata", 1957.
K. Miyazawa, et al., Bulletin of the Japanese Society of Scientific Fisheries, vol. 35, No. 12, pp. 1215–1219, "Aminosulfonic Acids in Six Species of Marine Algae", 1969.

* cited by examiner

*Primary Examiner*—Susan D. Coe
(74) *Attorney, Agent, or Firm*—Oblon, Spivak, McClelland, Maier & Neustadt, P.C.

(57) ABSTRACT

The present invention discloses an anti-obesity agent comprising:

D-cysteinolic acid represented by Formula I, as an active ingredient:

Formula I:

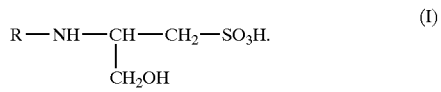

13 Claims, 1 Drawing Sheet

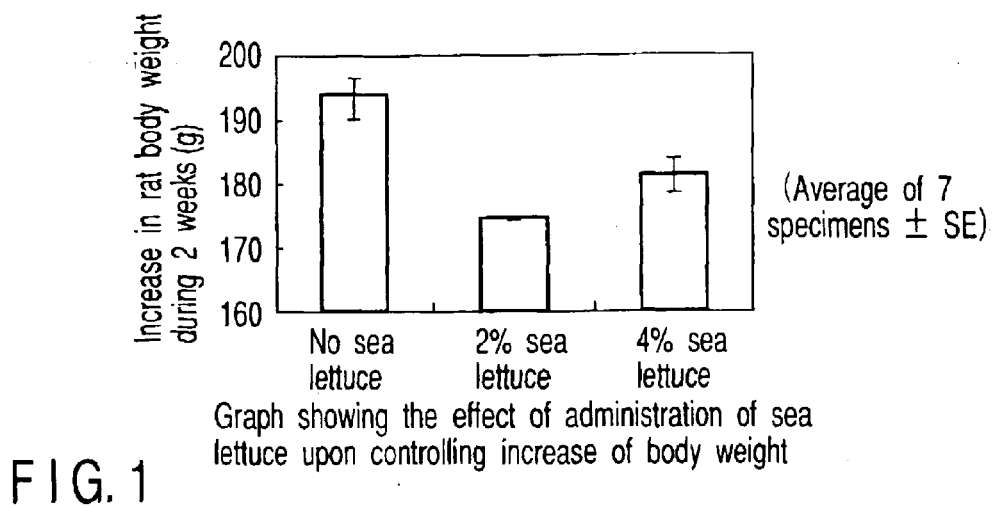
FIG. 1 Graph showing the effect of administration of sea lettuce upon controlling increase of body weight
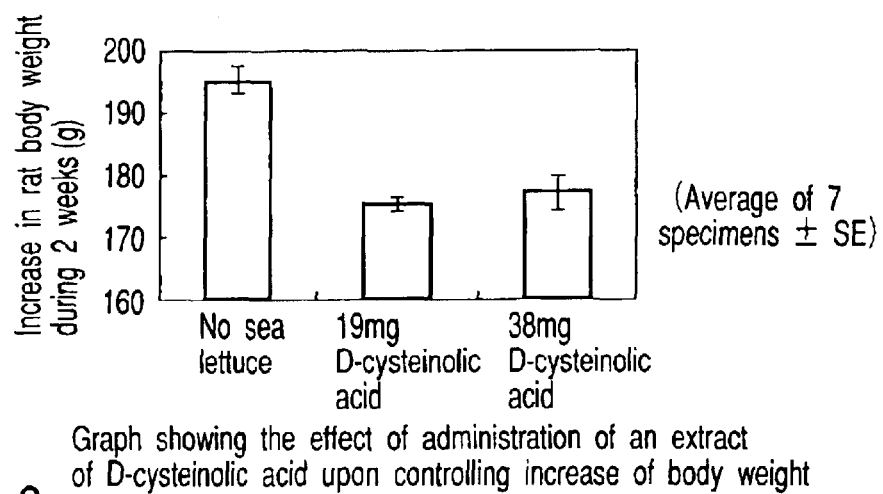
FIG. 2 Graph showing the effect of administration of an extract of D-cysteinolic acid upon controlling increase of body weight
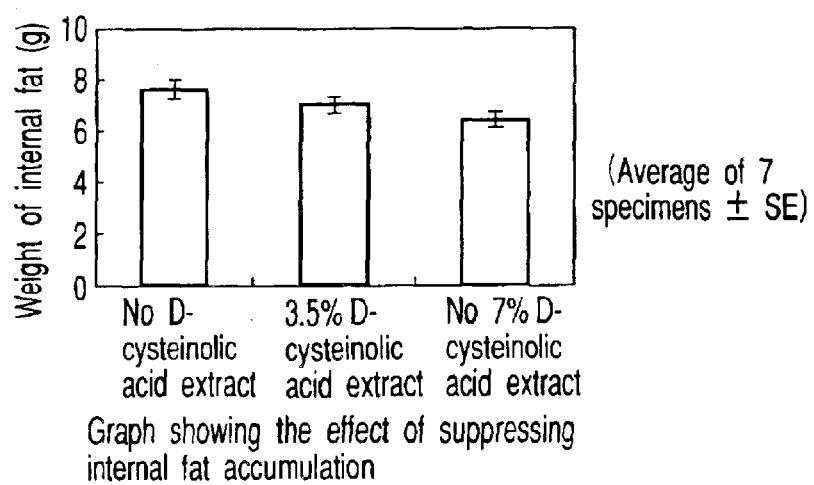
FIG. 3 Graph showing the effect of suppressing internal fat accumulation

HEALTH FOOD AND PREPARATION HAVING AN ANTI-OBESITY EFFECT

CROSS REFERENCE TO RELATED APPLICATIONS

This is a continuation application of U.S. application Ser. No. 10/186,702, filed on Jul. 2, 2002, now abandoned.

This application is based upon and claims the benefit of priority from prior Japanese Patent Applications No. 2001-226298 filed Jul. 26, 2001; and No. 2001-353609 filed Nov. 19, 2001, the entire contents of both of which are incorporated herein by reference.

BACKGROUND OF THE INVENTION

1. Field of the Invention

The present invention relates to an anti-obesity agent, food and pharmaceutical product containing a component suppressing adipogenesis, which is used as a raw material for pharmaceutical products, and pharmaceutical compositions as well as an additive for health foods and health beverages.

2. Description of the Related Art

D-cysteinolic acid ($C_3H_9NO_4S$: molecular weight: 155) was first isolated from red algae and identified by B. Wickberg in 1957 (Acta Chem Scand 11, 506 (1957)). In 1963, Itoh (University of Hiroshima) found that D-cysteinolic acid is also present in green algae and brown algae of seaweed (Bull. Jpn. Scient. Fish., 29, 771 (1963)). Recently, it was found that sardine contain D-cysteinolic acid. Since D-cysteinolic acid has an anti-clotting effect, its use as a raw material for pharmaceutical products has been expected. Indeed, an invention directed to thrombosis treatment and a preventive drug for thrombosis using D-cysteinolic acid from sardine has already been filed under Japanese Patent Application Publication No. 61-47880. Also, an invention directed to a cholesterol-reducing drug using D-cysteinolic acid or a cysteinolic acid/bile acid conjugate has been filed under Japanese Patent Application Publication No. 3-49113.

Under these circumstances, the present inventors found that sea lettuce (ulva,) produced by culturing can be effectively used to commercially produce D-cysteinolic acid. Such a method and device have already been filed as an invention under Japanese Patent Application Publication No. 11-222470. Furthermore, the invention directed to the effect of D-cysteinolic acid for preventing adipogenesis of neutral fat and lipoperoxide has been filed under Japanese Patent Application Publication No. 2000-202404.

That is all we know about D-cysteinolic acid. So far, most of the physiological activities of D-cysteinolic acid itself remain unknown. Since an effective physiological activity has not yet been found, the use of D-cysteinolic acid has been limited within a narrow range. Accordingly, the commercial development of D-cysteinolic acid has been delayed.

On the other hand, lately, the diet of Japanese people has been gradually westernized (toward a high fat diet). As a result, the accumulation of fat on not only blood vessels but also internal organs such as the intestines and the intestinal tract has been increasingly observed in many people. Such accumulation of fat causes adult diseases such as obesity, leading to serious problems. Therefore, the development of a safe compound having an anti-obesity effect has been strongly desired.

BRIEF SUMMARY OF THE INVENTION

In view of the aforementioned circumstances, an object of the present invention is to solve problems of the prior art. More specifically, the object of the present invention is to provide a compound being safe for humans and animals including farm animals and having an effect of suppressing an increase in body weight and to provide an anti-obesity agent containing such a compound as an active ingredient.

A further object of the present invention is to provide a pharmaceutical composition, a cosmetic material, a cosmetic, and a food containing such an, anti-obesity agent as an active ingredient.

On the other hand, another object of the present invention is to develop the use of sea lettuce and D-cysteinolic acid derived from sea lettuce.

The aforementioned objects are attained by the present invention below, namely, an anti-obesity agent comprising D-cysteinolic acid represented by Formula-I, as an active ingredient:

Formula I

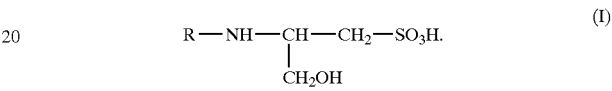

BRIEF DESCRIPTION OF THE SEVERAL VIEWS OF THE DRAWING

FIG. 1 is a graph showing the effect of sea lettuce powder upon the increase of rat's body weight;

FIG. 2 is a graph showing the effect of an extract of D-cysteinolic acid upon the increase of rat's body weight; and FIG. 3 is a graph showing the effect of D-cysteinolic acid upon the accumulation of fat within the rat's body.

DETAILED DESCRIPTION OF THE INVENTION

The present inventors have made intensive studies on an effective method for using D-cysteinolic acid derived from sea lettuce. As a result, they found that D-cysteinolic acid has a novel effect of significantly suppressing obesity. Based on such a novel finding, the present invention was attained.

According to a first aspect of the present invention, there is provided an anti-obesity agent containing D-cysteinolic acid represented by Formula I, as an active ingredient.

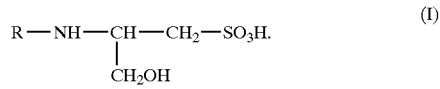

D-cysteinolic acid is capable of suppressing not only the increase of body weight but also the accumulation of fat within the body. Such a function of D-cysteinolic acid conceivably comes from the ability of D-cysteinolic acid for reducing the blood concentration and intracellular accumulation of natural fat originated from meal.

D-cysteinolic acid used in the present invention may be either extracted from a natural substance or synthesized, and preferably, commercially produced from sea lettuce. However, the production of D-cysteinolic acid is not limited to these methods.

A method of producing D-cysteinolic acid from sea lettuce is as follows. Sea lettuce is collected from sea, cultured, recovered, dried, and extracted with an appropriate solvent to-obtain D-cysteinolic acid, which is further purified (see Japanese Patent Application Publication No. 11-222470).

In particular, the present inventors found that a large amount (about 0.1 to 0.6% by dry weight) of D-cysteinolic acid is present in limited individuals of sterile sea lettuce (Ula Lactuca) produced by culturing throughout the year. The method and the apparatus for producing D-cysteinolic acid from such sea lettuce have been previously filed as Japanese Patent Application Publication No. 11-222470. Hence, it is preferable that the sea lettuce strain reported in Japanese Patent Application Publication No. 11-222470 should be used in accordance with an aspect of the present invention.

According to an aspect of the present invention, sea lettuce and an extract of D-cysteinolic acid having an anti-obesity effect may be used as a prophylactic agent or therapeutic agent in a wide range from internal medicine to surgery. The sea lettuce and an extract of D-cysteinolic acid according to the present invention may be used as anti-obesity agent in laboratories in the various fields, for example, medicine and pharmacology. The anti-obesity agent of the present invention inhibits obesity, thereby exhibiting excellent prophylaxis and therapeutic effect upon hyperlipemia and the like.

According to an aspect of the present invention, there is provided an anti-obesity agent containing D-cysteinolic acid as an effective component. The anti-obesity agent of the present invention has D-cysteinolic acid as an active ingredient. The anti-obesity agent of the present invention may contain desired substances, such as an excipient, other than D-cysteinolic acid and another active ingredient.

According to an aspect of the present invention, there is provided a pharmaceutical composition comprising D-cysteinolic acid as an active ingredient. The composition of the present invention may be used as a prophylactic or therapeutic agent for diseases associated with or ascribed to obesity. The pharmaceutical composition of the present invention will be described later more specifically.

According to an aspect of the present invention, there is provided a food comprising D-cysteinolic acid as an active ingredient. The food containing D-cysteinolic acid of the present invention may be used as nutritional enriched food or supplement food for special use. The food of the present invention will be described later more specifically.

Now, the pharmaceutical composition according to the present invention will be described below.

The pharmaceutical composition of the present invention may contain various other active ingredients having a therapeutic and/or prophylactic effect together D-cysteinolic acid as the active ingredient of the present invention.

The pharmaceutical composition of the present invention contains D-cysteinolic acid in an effective amount, for example, within the range of about 0.25 mg/kg to about 50 mg/kg weight per dose. The dose per day may be administered once or divided into several times in a day. More accurately, the dose may be varied in a wide range depending upon administration route, dose form, the symptom and weight of an object to be treated. Thus, the dose must be empirically selected and determined under the responsibility of a doctor or a veterinarian.

When an active ingredient with a high purity is administered, any administration route may be used as long as the active ingredient can be effectively delivered to a proper and desired body site. The active ingredient may be administered orally or non-orally (parenteral), more specifically, through any route including per rectum, percutaneously, subcutaneously, intravenously, urethrally, intramuscularly, nasally, intraperitoneally, and ophthalmologically. Of them, oral administration is the most preferable. When the active ingredient with a low purity is administered, in other words, when sea lettuce and the extract from sea lettuce are used as a main component, oral administration is exclusively used.

Typically, a pharmaceutical composition of the present invention contains the active ingredient of the present invention in combination with a pharmaceutically acceptable carrier. More specifically, the pharmaceutical composition may be manufactured by mixing the extract from sea lettuce into a pharmaceutically acceptable excipient and a carrier containing an auxiliary agent. Such a pharmaceutical composition may be manufactured by a well-known method including general mixing, dilution with a carrier, and encapsulating into a carrier. The pharmaceutical composition thus prepared may be enwrapped with paper or put into an ampule, capsule, or other containers. When a carrier is a diluent, the carrier may be a medium for extracting an active ingredient, a solid, semisolid or a liquid material possibly serving as an excipient or a medium. As a suitable carrier, water, a salt solution, castor oil, gelatin, lactose, alcohol, polyethylene glycol, magnesium stearate, amylose, pentaerythritol fatty ester, talc, silicic acid, fatty acid monoglyceride, fatty acid diglyceride, hydroxymethyl cellulose, polyvinyl pyrrolidine, and the like. However, the carrier is not limited to the aforementioned substances.

A pharmaceutical composition according to the present invention may be sterilized as needed. If necessary, any auxiliary agent, emulsifier, osmoregulatory salt, buffer, colorant and/or the like may be further added to the pharmaceutical composition as long as they are nontoxically mixed with the extract of the active agent.

The pharmaceutical composition according to the present invention to be used in a parenteral agent may be provided in the form of an aqueous injection solution, an aqueous injection suspension, or an oily injection suspension as long as it may be a pharmacologically parenteral form.

Now, the food of the present invention will be explained below. According to an aspect of the present invention, there is provided a food containing D-cysteinolic acid as an active ingredient. According to an aspect of the present invention, D-cysteinolic acid may be added to any type of food and any shape of food as an additive having an anti-obesity effect, that is, an effect of suppressing an increase of body weight. According to an aspect of the present invention, D-cysteinolic acid, sea lettuce, or an extract of D-cysteinolic acid may be added to food as an additive to provide a health food, a supplemental food or a nutritional enriched food.

According to an aspect of the present invention, there is provided a food containing D-cysteinolic acid, sea lettuce, or a D-cysteinolic acid extract. By adding D-cysteinolic acid to a food containing no D-cysteinolic acid (or containing a small amount of D-cysteinolic acid) and giving the food to a healthy individual, it is possible to suppress weight-increase of the individual. In this manner, the food of the present invention can contribute to maintaining individual constantly in good health. In other words, diseases associated with obesity (increase of body weight) such as diabetes, hyperlipemia, arteriosclerosis can be gently prevented simply by taking food. Accordingly, the food of the present invention can contribute to maintaining of good health and improving physical condition of an individual.

When an individual suffering from a disease associated with obesity such as diabetes, hyperlipemia, or arteriosclerosis takes the food of the present invention, it is possible to suppress the increase in body weight of the individual, facilitating the effect of the medical treatment applied by a doctor or a veterinarian.

D-cysteinolic acid is desirably added to the food of the present invention in an appropriate amount within the range suitable as food. As known to one skilled in the art, the composition of the food according to the present invention to be given to an individual suffering from the aforementioned disease must be prepared with care so as not to negatively affect the disorder. D-cysteinolic acid and/or sea lettuce or an extract from sea lettuce containing D-cysteinolic acid as an active ingredient may be added to food such as rices, beans, wheats, wheat flours, starch, sugar, starch sugar, breads, noodles, sweets, edible oils, dairy products (icecream, butter, cheese, lactic acid bacteria beverages), refreshing drinks, beans products, agricultural processed products (fruit beverages, canned foods, jams, dry fruits, etc.), fermented foods (liquors, edible vinegar, soy sauce, soybean paste, Worcester sauce, fermented soybeans, pickles etc.), meat products (sausage, canned ham, bacon; etc.), egg products, various frozen foods, dry foods, sea foods, precooked foods, boil-in-the-bag foods, enzyme products, and seasonings. However, the food of the present invention is not limited to these. Such an active ingredient can be added to food by any known method to one skilled in the art.

EXAMPLES

The present invention will be explained more specifically with reference to Examples, which only illustrate the present invention and therefore should not be construed as limiting the scope of the present invention.

Example 1

Sea lettuce (Ula lactuca MH1-ATRC-1 stain) was obtained from the seashore near Hakkei-jima (Kanazawa ward, Yokohama city). The obtained sea lettuce was cultured in sea water containing a dissolved nitrogen of about 1.1 ppm in concentration in a culture vessel (40 L) formed of transparent acrylic resin arranged outdoors. The culturing was performed while air was supplied to the culture vessel at a velocity of 0.15 L/L (volume of sea water) per minute and sea water was replaced at a flow rate of 2 L/hr to supply the dissolved nitrogen to sea lettuce. After pre-culturing was performed for 3 days, sea lettuce was cultured for 11 days. The proliferation rate during the culture was 15 g (dry weight)/m$^2$ per day.

The sea lettuce thus cultured was washed with pure water, dehydrated, and dried at room temperature. As a result, 20 g by dry weight of sea lettuce was obtained. The sea lettuce was soaked in an aqueous 60% (v/v) % ethanol solution and subjected to extraction in a warm bath. The extract was concentrated under a reduced pressure, degreased and decolored with diethylether to obtain a translucent aqueous solution. Subsequently, the obtained solution was treated with activated carbon (charcoal). After an extra pigment was absorbed by the charcoal, the resultant solution was filtrated to obtain a transparent aqueous solution. The filtrate was concentrated to obtain D-cysteinolic acid having a purity of 40%.

Sterile sea lettuce MH1-ATRC-1 is a strain, for the first time, isolated and identified by the present inventors. The present inventors have tried to deposit the strain at National Institute of Bioscience and Human-Technology, Agency of Industrial Science and Technology. However, the agency rejected the deposition by reason that the strain belongs to green algae. At present, the strain is maintained under the administration of the Advanced Technology Research Center, MITSUBISHI HEAVY INDUSTRIES, LTD.

Example 2

The effect of sea lettuce and D-cysteinolic acid for suppressing increase of body weight in rats Sea lettuce was pulverized into pieces of about 20 $\mu$m diameter. The pulverized sea lettuce was mixed with a fat-containing diet containing 10% by weight of a fat component. In this way, diets containing sea lettuce in amounts of 1, 2 and 4% by weight of the total amount were prepared. The diets were given to SD male rats for 2 weeks and thereafter weight change was examined. To explained more specifically, a diet containing no sea lettuce, a diet containing 2% of sea lettuce, a diet containing 4% of sea lettuce were respectively given to three groups each consisting of 7 SD male rats.

The results of weight change are shown in FIG. 1. In each group, the increased weights of 7 rats during 2 weeks are averaged and expressed as an average value ± standard deviation in the graph. The group fed with sea lettuce exhibits 8–10% suppression of weight increase as compared to the group fed with no sea lettuce. In this case, the sea lettuce contained 0.56% by weight of D-cysteinolic acid.

Subsequently, the same experiment as above was performed except that the freeze-dried D-cysteinolic acid extract with a purity of 40% (extracted in accordance with the aforementioned method) was used in place of the pulverized sea lettuce. The concentration of D-cysteinolic acid extract to be administered was adjusted by mixing the extract with the fat-containing diet to prepare a diet containing D-cysteinolic acid in such an amount that the rat takes at least 5 mg/day of D-cysteinolic acid. The diet containing D-cysteinolic acid extract was orally administered to rats for 2 weeks so as to give D-cysteinolic acid in amounts of 0, 19 and 38 mg/g weight per rat.

After 2 weeks, the effect of D-cysteinolic acid extract for suppressing weight increase was evaluated in the same manner as mentioned above. The results are shown in FIG. 2. Compared to the rat group fed with no D-cysteinolic acid extract, the rat group fed with D-cysteinolic acid extract in amounts of 0, 19 and 18 mg exhibits 9% decrease in weight increase. No abnormality was observed with regard to fur quality, eating behavior, or excretion (such as diarrhea) of rats in the two experiments mentioned above, demonstrating that such a weight increase suppressing activity is not caused by excretion abnormality and eating-behavior abnormality. Note that data contained in each graph is expressed as an average weight increase of 7 SD rats ± a standard deviation.

The results mentioned above clearly shows that sea lettuce or a sea lettuce extract containing D-cysteinolic acid as an active ingredient has an effect of suppressing weight increase. The fact that D-cysteinolic acid can suppress weight increase in an animal is for the first time revealed by the present inventors through the experiments using living whole animals. When the results are translated into human terms on the assumption that the life span of a rat is about 3 years, the effect obtained in the rat is equivalent to reducing weight by 10% over six months to one year in a human. The weight-increase suppressing function of D-cysteinolic acid is considered ideal since any burden is given to a body from the nutritional and medical points of view.

The present inventors found and revealed that D-cysteinolic acid has the effect of greatly suppressing neutral fat (triglyceride) in cultured HepG2 cells of a human liver model. Based on this finding, they achieved an invention and filed under Japanese patent application No. 2000-202404.

Also in the experiments regarding the present invention, SD rats were fed with sea lettuce or an extracted D-cysteinolic acid and the amount of blood neutral fat was measured. As a result, the amount of neutral fat reduced up to 25 to 30% both in the group fed with sea lettuce and the group fed with D-cysteinolic acid extract. The aforementioned data suggests that D-cysteinolic acid merely has a function of suppressing the accumulation of neutral fat originated from fat contained in a meal but has a function of reducing the amount of blood neutral fat.

Furthermore, D-cysteinolic acid extract was mixed into a diet in amounts of 0, 3.5, and 7% by weight of the total amount and fed to SD rats. After 2 weeks, the amount of the internal fat of each rat was determined by weighing a total weight of the fat attached to the small intestine, suprarenal gland and testis. The results are shown in FIG. 3. The amount of internal fat in the group fed with D-cysteinolic acid (crude D-cysteinolic acid) extract is smaller than that the group fed with no D-cysteinolic acid. This fact clearly shows that D-cysteinolic acid suppresses the amount of fat accumulation.

The mechanism how to suppress the accumulation of fat is a problem to be analyzed. It is so far conceivable that the accumulation of fat originated from a meal is reduced by the function of D-cysteinolic acid for reducing the amount of neutral fat in blood and a cell, producing the effect of suppressing weight increase.

The experiments above clearly shows that D-cysteinolic acid is a substance having a function of suppressing the accumulation of internal fat and suppressing the increase of body weight. Also, D-cysteinolic acid can be used as an additive such as health foods, pharmaceutical products and cosmetics.

According to the present invention, the activity of D-cysteinolic acid is used to suppress obesity, that is, the increase of body weight, causing various diseases and aging.

According to the present invention, there is provided a novel use of D-cysteinolic acid, that is, a prophylaxis use of D-cysteinolic acid, which is a completely safe product because of an extract from sea lettuce. In addition, there is provided a newly found use of dry sea lettuce or an extract from sea lettuce.

In the prior art, an agent for suppressing the accumulation of neutral fat strongly connected to obesity has been developed as a pharmaceutical product in quite a few research institutions. However, there are no drug and foodstuff derived from natural food and having few side effects, for use in preventive medicine and health maintenance. Therefore, it is the present invention to first provide such a drug and foodstuff derived from natural food for use in preventive medicine and health maintenance. The entire contents of the documents cited in this text are incorporated herein by reference.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of treating or suppressing obesity in a subject in need thereof, comprising administering to the subject an effective amount of an anti-obesity agent comprising:

D-cysteinolic acid represented by Formula I, as an active ingredient:

Formula I:

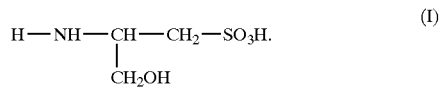

2. The method according to claim 1, wherein the anti-obesity agent is administered in the form of a pharmaceutical composition.

3. The method according to claim 1, wherein the anti-obesity agent is administered in the form of a cosmetic composition.

4. The method according to claim 1, wherein the anti-obesity agent is administered in the form of a food composition.

5. A method of treating or suppressing obesity in a subject in need thereof, comprising administering to the subject an effective amount of an anti-obesity agent comprising a material selected from the group consisting of sea lettuce and an extract from sea lettuce as an active ingredient.

6. The method according to claim 5, wherein the anti-obesity agent is administered in the form of a pharmaceutical composition.

7. The method according to claim 5, wherein the anti-obesity agent is administered in the form of a cosmetic composition.

8. The method according to claim 5, wherein the anti-obesity agent is administered in the form of a food composition.

9. A method of treating or suppressing obesity in a subject in need thereof, comprising administering to the subject an effective amount of an anti-obesity agent comprising an extract from sea lettuce obtained with water at a temperature of 50–70° C., as an active ingredient.

10. The method according to claim 9, wherein the anti-obesity agent is administered in the form of a pharmaceutical composition.

11. The method according to claim 9, wherein the anti-obesity agent is administered in the form of a cosmetic composition.

12. The method according to claim 9, wherein the anti-obesity agent is administered in the form of a food composition.

13. A method of treating or suppressing obesity in a subject in need thereof, comprising administering to the subject an effective amount of an anti-obesity agent comprising at least one material selected from the group consisting of D-cysteinolic acid, represented by Formula I:

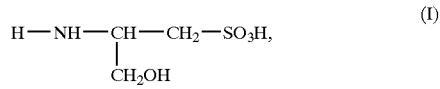

sea lettuce, and an extract from sea lettuce, as an active ingredient.

* * * * *